United States Patent
Nagata et al.

(10) Patent No.: US 11,161,806 B2
(45) Date of Patent: Nov. 2, 2021

(54) PROCESS FOR PRODUCING COMPOUND

(71) Applicant: ASAHI KASEI KABUSHIKI KAISHA, Tokyo (JP)

(72) Inventors: Dai Nagata, Tokyo (JP); Sho Tamura, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/604,485

(22) PCT Filed: Jun. 19, 2018

(86) PCT No.: PCT/JP2018/023223
§ 371 (c)(1),
(2) Date: Oct. 10, 2019

(87) PCT Pub. No.: WO2018/235798
PCT Pub. Date: Dec. 27, 2018

(65) Prior Publication Data
US 2020/0165196 A1 May 28, 2020

(30) Foreign Application Priority Data

Jun. 19, 2017 (JP) .............................. JP2017-119459

(51) Int. Cl.
| | |
|---|---|
| C07C 253/24 | (2006.01) |
| B01J 8/24 | (2006.01) |
| B01J 23/00 | (2006.01) |
| B01J 8/00 | (2006.01) |
| B01J 35/08 | (2006.01) |
| C07C 255/08 | (2006.01) |

(52) U.S. Cl.
CPC .............. *C07C 253/24* (2013.01); *B01J 8/24* (2013.01); *B01J 23/002* (2013.01); *B01J 8/0055* (2013.01); *B01J 35/08* (2013.01); *C07C 255/08* (2013.01)

(58) Field of Classification Search
None
See application file for complete search history.

(56) References Cited

U.S. PATENT DOCUMENTS

| | | |
|---|---|---|
| 4,370,279 A | 1/1983 | Sasaki et al. |
| 4,691,031 A | 9/1987 | Suciu et al. |
| 2013/0289298 A1 | 10/2013 | Tateno et al. |
| 2014/0148610 A1 | 5/2014 | Brazdil, Jr. et al. |
| 2015/0152024 A1 | 6/2015 | Iitsuka et al. |
| 2016/0256848 A1 | 9/2016 | McDonel et al. |

FOREIGN PATENT DOCUMENTS

| | | |
|---|---|---|
| JP | 57-65329 A | 4/1982 |
| JP | 10-263406 A | 10/1998 |
| JP | 11-500062 A | 1/1999 |
| JP | 2001-276618 A | 10/2001 |
| JP | 2002-355547 A | 12/2002 |
| JP | 2006-263715 A | 10/2006 |
| JP | 2015-536821 A | 12/2015 |
| WO | WO 2012/096367 A1 | 7/2012 |
| WO | WO 2014/025021 A1 | 2/2014 |

OTHER PUBLICATIONS

European Supplementary Search Report for European Application No. 18821560.2, dated Jun. 9, 2020.
International Search Report for International Application No. PCT/JP2018/023223, dated Aug. 14, 2018, with English translation.
Written Opinion of the International Searching Authority for International Application No. PCT/JP2018/023223, dated Aug. 14, 2018.
Werther et al., "Catalyst Attrition in Fluidized-Bed Systems," AIChE Journal, vol. 45, No. 9, Sep. 1999, pp. 2001-2010, 10 pages total.

*Primary Examiner* — Joseph R Kosack
(74) *Attorney, Agent, or Firm* — Birch, Stewart, Kolasch & Birch, LLP.

(57) ABSTRACT

A process for producing a compound by use of a fluidized bed reactor comprising an internal space having a catalyst housed in a fluidizable manner therein, a first feed port into which a starting material gas comprising a hydrocarbon is fed to the fluidized bed reactor, a second feed port into which an oxygen-containing gas comprising oxygen is fed to the fluidized bed reactor, and a discharge port into which a reaction product gas is discharged from the fluidized bed reactor, including a reaction step of subjecting the hydrocarbon to a vapor phase catalytic oxidation reaction or a vapor phase catalytic ammoxidation reaction in the presence of the catalyst in the internal space to produce the corresponding unsaturated acid or unsaturated nitrile, respectively, wherein in the reaction step, a linear velocity (m/sec) of the starting material gas at the first feed port is adjusted against a degree of abrasion resistance (%) of the catalyst so as to satisfy a prescribed relation between them.

3 Claims, 2 Drawing Sheets

PROCESS FOR PRODUCING COMPOUND

TECHNICAL FIELD

The present invention relates to a process for producing a compound.

BACKGROUND ART

Conventionally, a fluidized bed reactor has been widely used when an alkane and/or an alkene is subjected to a vapor phase catalytic ammoxidation reaction in the presence of a metal composite oxide catalyst. In a fluidized bed reactor used on an industrial scale, the production operation is continuously carried out for a long period of time, and therefore, a decrease in catalytic activity exerting influence on the reaction yield, reduction of the amount of a catalyst packed due to outflow of the catalyst and a change in particle size distribution of a catalyst or the like are brought about. On that account, for the purpose of improving a reaction yield of unsaturated nitrile, development of catalysts, improvement in internal equipment of the reactor, etc. have been made.

For example, in Patent Literature 1, a method of using fine particles of a primary calcined product containing molybdenum, bismuth, iron and silica is disclosed for the purpose of providing a process for producing a catalyst having sufficient strength (abrasion resistance).

CITATION LIST

Patent Literature

Patent Literature 1: Japanese Patent Laid-Open No. 2006-263715

SUMMARY OF INVENTION

Technical Problem

When a catalyst having low abrasion resistance is used, there is a problem that the catalyst is slowly crushed or a finely divided catalyst flows out of a fluidized bed reactor to reduce the catalytic amount in the fluidized bed reactor, whereby a reaction yield of a compound is reduced. On the other hand, it has been found that when a catalyst having high abrasion resistance is used, damage to the interior of the fluidized bed reactor is observed. Accumulation of damage to the interior of the fluidized bed reactor can exert various influences such that destruction of the reactor that is greatly dangerous is brought about and a decrease in accuracy of the reaction control due to an increase in diameter of a feed port for a starting material gas, namely a harmful effect in actual operation, can be brought about. In order not to damage the interior of the fluidized bed reactor in the case where a catalyst having high abrasion resistance is used, it is thought that the linear velocities of various gases fed are decreased so that the catalyst should not strongly collide with the interior of the fluidized bed reactor. However, decrease in linear velocities of gases exerts direct influence on the reduction of fluidity of the catalyst, and as a result, reduction of the reaction yield of a compound is brought about.

The present invention has been made in the light of the above problem, and it is an object of the present invention to provide a process for producing a compound in which the compound can be obtained in a high yield without causing damage to a reactor while suppressing scattering of a catalyst.

Solution to Problem

In order to solve the above problem, the present inventors have earnestly studied. As a result, they have found that by controlling a hardness of the catalyst and a linear velocity of the staring material gas, the above problem can be solved, and they have completed the present invention.

That is to say, the present invention is as follows.

[1]

A process for producing a compound by use of a fluidized bed reactor comprising an internal space having a catalyst housed in a fluidizable manner therein, a first feed port into which a starting material gas comprising a hydrocarbon is fed to the internal space, a second feed port into which an oxygen-containing gas comprising oxygen is fed to the internal space, and a discharge port into which a reaction product gas is discharged from the internal space, comprising a reaction step of subjecting the hydrocarbon to a vapor phase catalytic oxidation reaction or a vapor phase catalytic ammoxidation reaction in the presence of the catalyst in the internal space to produce the corresponding unsaturated acid or unsaturated nitrile, respectively, wherein in the reaction step, a linear velocity (m/sec) of the starting material gas at the first feed port is adjusted against a degree of abrasion resistance (%) of the catalyst so as to satisfy the condition represented by the following formula (1) or (2):

condition (1): when the degree of abrasion resistance (%) of the catalyst is not less than 0 and not more than 4, $$5 \leq \text{linear velocity (m/sec)} \leq 12.5 \times \text{degree of abrasion resistance (\%)} + 100$$

condition (2): when the degree of abrasion resistance (%) of the catalyst is more than 4 and not more than 62, $$5 \leq \text{linear velocity (m/sec)} \leq -2.5 \times \text{degree of abrasion resistance (\%)} + 160.$$

[2]

The process for producing the compound according to [1], wherein a hollow particle ratio (%) of the catalyst is not more than 25%.

[3]

The process for producing the compound according to [1] or [2], wherein the degree of abrasion resistance (%) is not less than 1 and not more than 10.

[4]

The process for producing the compound according to any one of [1] to [3], wherein the hydrocarbon is an alkane and/or an alkene.

Advantageous Effects of Invention

According to the present invention, a process for producing a compound in which the compound can be obtained in a high yield without causing damage to a reactor while suppressing scattering of a catalyst can be provided.

DESCRIPTION OF EMBODIMENTS

Figure 1:
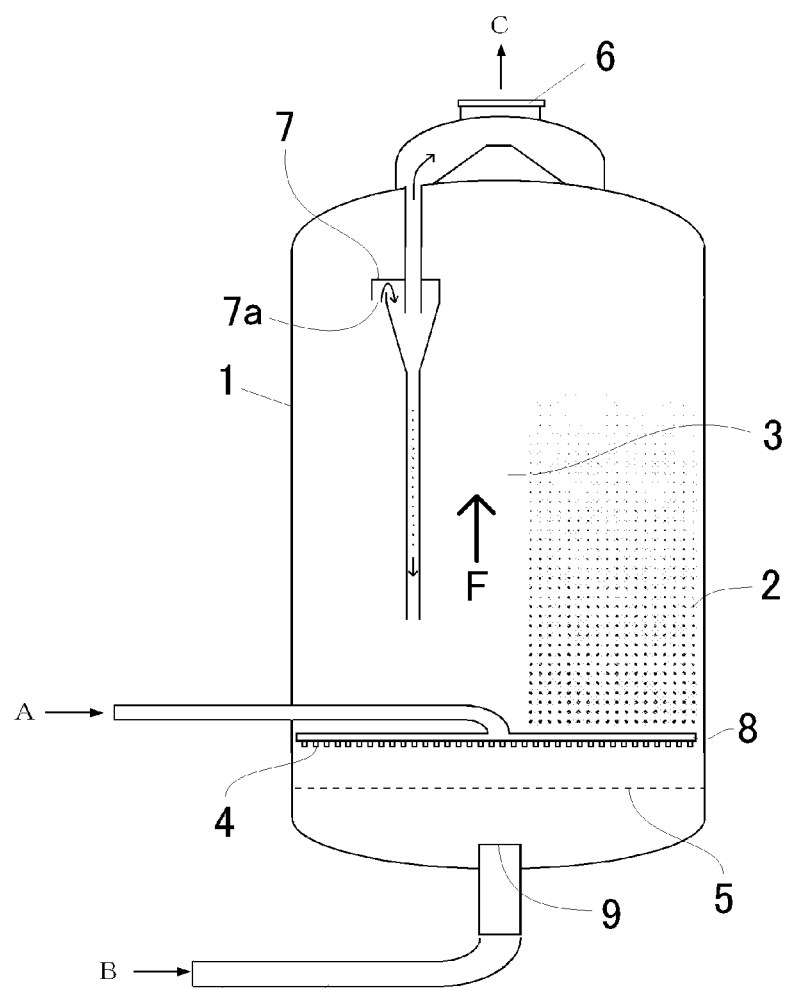
FIG. 1 shows a schematic sectional view of a fluidized bed reactor which can be used in the process for producing unsaturated nitrile of the present embodiment.

An embodiment of the present invention (referred to as the "present embodiment" hereinafter) is described below in detail, but the present invention is not limited to this and can be variously modified without departing from the spirit of the present invention. In the drawings, the same elements are denoted by the same reference characters, and a repeated description thereof may be omitted. Unless otherwise noted, the positional relations such as up and down and left and right are based on the positional relations shown in the drawings. Further, the dimensional ratios in the drawings are not limited to the ratios illustrated.

[Process for Producing Compound]

The process for producing a compound of the present embodiment by use of a fluidized bed reactor comprising an internal space having a catalyst housed in a fluidizable manner therein, a first feed port into which a starting material gas comprising a hydrocarbon is fed to the fluidized bed reactor, a second feed port into which an oxygen-containing gas comprising oxygen is fed to the fluidized bed reactor, and a discharge port into which a reaction product gas is discharged from the fluidized bed reactor, comprises a reaction step of subjecting the hydrocarbon to a vapor phase catalytic oxidation reaction or a vapor phase catalytic ammoxidation reaction in the presence of the catalyst in the internal space to produce the corresponding unsaturated acid or unsaturated nitrile, respectively, wherein in the reaction step, a linear velocity (m/sec) of the starting material gas at the first feed port is adjusted against a degree of abrasion resistance (%) of the catalyst so as to satisfy the condition represented by the following formula (1) or (2):

condition (1): when the degree of abrasion resistance (%) of the catalyst is not less than 0 and not more than 4, $$5 \leq \text{linear velocity (m/sec)} \leq 12.5 \times \text{degree of abrasion resistance (\%)} + 100$$

condition (2): when the degree of abrasion resistance (%) of the catalyst is more than 4 and not more than 62, $$5 \leq \text{linear velocity (m/sec)} \leq -2.5 \times \text{degree of abrasion resistance (\%)} + 160.$$

[Fluidized Bed Reactor]

In FIG. 1, a schematic sectional view of a fluidized bed reactor which can be used in the present embodiment is shown. A fluidized bed reactor 1 is installed in such a manner that the direction of an arrow F becomes a substantially vertical direction to the ground surface, and has an internal space 3 having a catalyst 2 housed in a fluidizable manner therein, a first feed port 4 into which a starting material gas A containing a hydrocarbon is fed to the fluidized bed reactor 1, a second feed port 9 into which an oxygen-containing gas B containing oxygen is fed to the fluidized bed reactor 1, and a discharge port 6 into which a reaction product gas C is discharged from the fluidized bed reactor 1. In the embodiment illustrated in FIG. 1, the starting material gas A containing a hydrocarbon is fed into the internal space 3 from the first feed port 4 through a dispersion tube 8, and the oxygen-containing gas B introduced from the second feed port 9 is dispersed in the internal space 3 by a dispersion plate 5. The starting material gas A to be fed from a plurality of the first feed ports 4 and the oxygen-containing gas B to be fed by being dispersed by a plurality of openings of the dispersion plate 5 are fed in such a manner that these gases face each other, and they are blended while being intermingled with each other.

The catalyst 2 is fluidized in the internal space 3 with a balance among the weight and the volume of the catalyst itself, the feed rates of the starting material gas A and the oxygen-containing gas B (flow rates in the direction of the arrow F), etc. The existing amount (distribution) of the catalyst 2 per unit space decreases toward the upper part from the lower part of the internal space 3 (in the direction of the arrow F).

The internal space 3 may have a cyclone 7 to separate and recover the catalyst 2 from the reaction product gas, and when necessary, may further have a cooling coil (not shown) to mainly remove heat of reaction of the lower space of the internal space 3 and thereby control the reaction temperature and a member (not shown) to control a superficial gas velocity in the internal space 3. The superficial gas velocity in the internal space 3 varies with a cross-sectional area of the internal space 3 (cross-sectional area in a direction orthogonally intersecting with the direction of the arrow F). For example, when an internal space 3 whose cross-sectional areas are not uniform is supposed, the superficial gas velocity decreases at a place having a large cross-sectional area, and the superficial gas velocity increases at a place having a small cross-sectional area. From the viewpoint of control of the superficial gas velocity at each place of the internal space 3, the member to control the superficial gas velocity is installed in the internal space 3, and the gas-flowable cross-sectional area at a place where the member to control the superficial gas velocity is installed is narrowed by a portion occupied by the member to control the superficial gas velocity, so that the superficial gas velocity at this place increases as compared with that at a place where the member to control the superficial gas velocity is not installed. Instead of installing the member to control the superficial gas velocity, a fluidized bed reactor 1 whose diameters are not uniform so that the cross-sectional area of the internal space 3 may vary at the desired place may be used.

The reaction product gas accompanied by the catalyst 2 enters the cyclone 7 through an inlet 7a. The catalyst 2 having entered the cyclone 7 falls downward in the internal space 3 so as to be spiral in a conical part of the cyclone 7, while the reaction product gas is guided to the discharge port 6 by a tube extending upward from the upper part of the cyclone 7. Below the conical part of the cyclone 7, a tube further extends downward in the internal space 3, and through this tube, the catalyst 2 is guided downward in the internal space 3.

[Reaction Step]

In the present embodiment, a reaction step of, using a fluidized bed reactor configured as above, subjecting the hydrocarbon to a vapor phase catalytic oxidation reaction or a vapor phase catalytic ammoxidation reaction in the presence of the catalyst in the internal space of the reactor to produce the corresponding unsaturated acid or unsaturated nitrile, respectively is carried out.

Examples of the hydrocarbons used herein include, but are not limited to, alkanes, such as methane, ethane, propane, n-butane and isobutane; and alkenes, such as ethylene, propylene, n-butylene and isobutylene. Of these, propane, isobutane, propylene and isobutylene are preferable, and propane and/or propylene is more preferable, from the viewpoint of values of the resulting nitrile compound as an intermediate material for chemicals.

In the starting material gas A, starting materials other than the hydrocarbon may be contained. Examples of such starting materials include ammonia, oxygen and air. As previously described, oxygen, air or the like can be fed as the oxygen-containing gas B separately from the staring material gas A.

The catalyst is not particularly limited as long as it is a solid catalyst usually used for the reaction, and such a catalyst is, for example, a metal oxide catalyst supported on silica or the like.

The hollow particle ratio of the catalyst is preferably not more than 25%, more preferably not more than 20%, and still more preferably not more than 17%. By specifying the hollow particle ratio of the catalyst within the above range, the abrasion resistance and the compression strength tend to become appropriate. Moreover, the fluidity of the catalyst in the fluidized bed reactor is improved, and the amount scattered is reduced. Here, the "hollow particle" refers to a particle in which an area occupied by a vacancy based on a sectional area of the particle is not less than 1% when a section of the particle is observed. A solid particle that is a concept opposite to the hollow particle refers to a particle in which the area occupied by a vacancy is less than 1% or a particle having no vacancy.

The hollow particle ratio refers to a value obtained by dividing the number of hollow particles observed by the number of all the particles observed and multiplying the resulting value by 100. A method for measuring the hollow particle ratio will be described in the Examples described later.

The degree of abrasion resistance of the catalyst is 0 to 43%, preferably 1 to 25%, more preferably 1 to 10%, and still more preferably 2 to 8%. By specifying the degree of abrasion resistance of the catalyst within the above range, the amount scattered tends to be further reduced.

Figure 2:
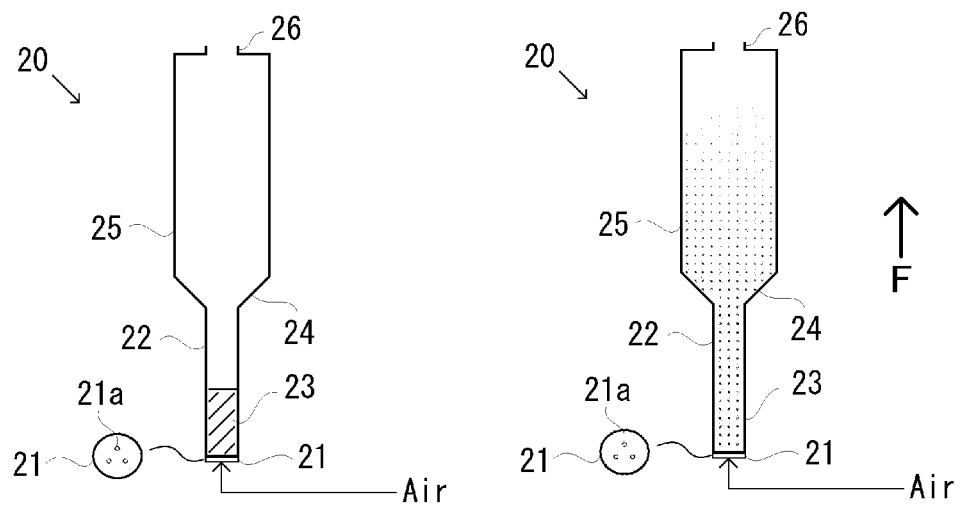
FIG. 2 shows a group of schematic views to illustrate a method for measuring a degree of abrasion resistance (%) of a catalyst.

A method for measuring the degree of abrasion resistance of the catalyst in the present embodiment is carried out using an apparatus for measuring the degree of abrasion resistance. In FIG. 2, schematic views illustrating the method for measuring the degree of abrasion resistance (%) of the catalyst using an apparatus for measuring the degree of abrasion resistance 20 are shown. The apparatus for measuring the degree of abrasion resistance 20 is configured to cause a gas to flow vertically upward from the vertically lower part (opposite direction to the arrow F) to make a catalyst fluidizable within the apparatus, the catalyst having been blown up by air that has been caused to flow into the apparatus, and the apparatus is configured such that the gas can flow out from the upper end of the apparatus. The catalyst having been blown up is slowly crushed by collision of catalyst particles with each other or collision of the catalyst with the inner wall of the apparatus, whereby the catalyst can be abraded. The catalyst whose weight has become below a certain level by the crushing is scattered outside the apparatus from the upper end of the apparatus, together with the gas. By evaluating a relation between a period of time in which the apparatus for measuring the degree of abrasion resistance is operated under the fixed gas inflow rate conditions and the amount scattered, the degree of abrasion resistance of the catalyst can be evaluated. Specifically, in the apparatus for measuring the degree of abrasion resistance 20, about 50 g of a catalyst 23 is weighed (mass of the catalyst is regarded as "initial input amount") and packed in a vertical tube 22 having an inner diameter of 1.5 inches and a length of 27.5 mm and equipped, at its bottom, with a hole-opened disc 21 having three orifices 21a each having an inner diameter of 0.016 inch. On the vertical tube 22, a cylinder 25 having an outer diameter of 5 inches and a length of 22 inches (also referred to as a "5-inch cylinder" hereinafter) is provided through a conical part 24. At the upper end of the cylinder 25, an opening 26 having an inner diameter of 1.2 inches is provided.

In the measurement of the degree of abrasion resistance of the catalyst, air is made to flow into the apparatus for 120 hours in such a manner that the linear velocity of a gas passing though the orifices 21a of the hole-opened disc 21 becomes the velocity of sound (340 m/s), whereby the catalyst is fluidized. Under the above conditions, the degree of abrasion resistance of the catalyst is defined by the following formula.

Degree of abrasion resistance (%)=(mass of catalyst scattered outside the system from top of 5-inch cylinder during the period from 5 hours to 120 hours)/(initial input amount−(mass of catalyst scattered outside the system from top of 5-inch cylinder during the period from 0 to 5 hours))×100

A method for controlling the degree of abrasion resistance (%) of the catalyst is not particularly restricted, and for example, a method for controlling it by the amount of a carrier contained in the catalyst can be mentioned. The content of the carrier in the catalyst is preferably 20 to 70 mass %, more preferably 40 to 65 mass %, and still more preferably 40 to 60 mass %, based on the total amount of the catalyst. By specifying the content of the carrier in the catalyst to not less than 20 mass %, mechanical strength of the catalyst is further improved, and the catalyst can be inhibited from being crushed and scattered. By specifying the content of the carrier in the catalyst to not more than 70 mass %, reduction of activity caused by an excessive amount of a carrier can be suppressed. Moreover, by allowing the content of the carrier in the catalyst to satisfy the above range, specific gravity of the catalyst becomes more appropriate, and a good fluidized state tends to be easily formed.

The carrier is not particularly restricted, and is, for example, a carrier containing silica as a main component. By allowing a carrier containing silica as a main component to support the catalyst, mechanical strength is further improved, and such a catalyst can be preferably used for the vapor phase catalytic ammoxidation reaction using a fluidized bed reactor.

[Linear Velocity of Starting Material Gas]

In the process for producing a compound of the present embodiment, in the above-described reaction step, the linear velocity of the starting material gas at the first feed port (m/sec, also referred to as "gas linear velocity" simply hereinafter) is adjusted against the degree of abrasion resistance (%) of the catalyst so as to satisfy the condition represented by the following formula (1) or (2). The "first feed port" is an opening at each tip of a plurality of nozzles when a dispersion tube 8 is provided, as shown in FIG. 1, and when a ring sparger is used, the first feed port is an opening of the sparger. The linear velocity (m/sec) can be calculated by dividing the total flow rate ($m^3$/sec) of a gas per time required for the gas to pass the first feed ports 4 by the total area ($m^2$) of the first feed ports 4. The starting material gas is, for example, a hydrocarbon gas in the oxidation reaction, and is, for example, a hydrocarbon gas or ammonia gas in the ammoxidation reaction.

Condition (1): when the degree of abrasion resistance (%) of the catalyst is not less than 0 and not more than 4, 5≤linear velocity (m/sec)≤12.5×degree of abrasion resistance (%)+100.

Condition (2): when the degree of abrasion resistance (%) of the catalyst is more than 4 and not more than 62, 5≤linear velocity (m/sec)≤−2.5×degree of abrasion resistance (%)+160.

When the degree of abrasion resistance (%) is not less than 0 and not more than 4, the catalyst is relatively hard. On that account, if the gas linear velocity is too high, erosion takes place, and the reactor is liable to be damaged. Accumulation of damage to the reactor can lead to troubles such that the diameter of the first feed port changes to alter the gas linear velocity and intermingling of the starting material gas and the oxygen-containing gas with each other cannot be normally carried out. On the other hand, if the gas linear velocity is too low, the fluidity of the catalyst in the fluidized bed is lowered, and this leads to reduction of a yield of a compound. On that account, when the degree of abrasion resistance (%) is not less than 0 and not more than 4, adjustment of the gas flow rate is carried out within the range satisfying the above condition (1).

When the degree of abrasion resistance (%) is more than 4 and not more than 62, the catalyst is relatively brittle. On that account, if the gas linear velocity is too high, the catalyst is crushed and abraded by the collision of catalyst particles with each other or the collision of the catalyst with the inner wall of the internal space. The crushed pieces of the catalyst and the catalyst having become smaller than a certain size can be scattered outside the internal space by the force of the gas flow rate. If the amount of the catalyst scattered increases, the catalytic amount in the internal space relatively decreases, and therefore, reduction of a yield of a compound is brought about. On the other hand, if the gas linear velocity is too low, the fluidity of the catalyst in the fluidized bed is lowered, and this leads to reduction of a yield of a compound. On that account, when the degree of abrasion resistance (%) is more than 4 and not more than 62, adjustment of the gas flow rate is carried out within the range satisfying the above condition (2).

A material generally used for the fluidized bed reactor is carbon steel, and from the relation to the hardness of this material, a value of 4% that is a boundary value of the degree of abrasion resistance (%) is determined.

A method for controlling the linear velocity (m/sec) of the starting material gas is not particularly restricted, and for example, the linear velocity can be controlled by increase/decrease in the area of the opening of the feed port, change of the reaction pressure in the internal space, change of the temperature of the interior of the reactor, increase/decrease in the amount of diluent nitrogen gas to be mixed with the starting material gas, etc.

EXAMPLES

The present invention is more specifically described below with reference to Examples and Comparative Examples. The present invention is in no way limited to the following Examples.

[Method for Measuring Degree of Abrasion Resistance of Catalyst]

In the measurement of the degree of abrasion resistance of the catalyst, an apparatus similar to that shown in FIG. 2 was used. Air was made to flow into the apparatus for 120 hours in such a manner that the linear velocity of a gas passing through orifices 21a of a hole-opened disc 21 became the velocity of sound (340 m/s), and the degree of abrasion resistance of the catalyst was calculated from the following formula.

Degree of abrasion resistance (%)=(mass of catalyst scattered outside the system from top of 5-inch cylinder during the period from 5 hours to 120 hours)/(initial input amount−(mass of catalyst scattered outside the system from top of 5-inch cylinder during the period from 0 to 5 hours))×100

[Evaluation of Hollow Particle Ratio]

The calcined catalyst particles were embedded in an epoxy resin. Subsequently, the resin with particles embedded therein was abraded to expose sections of the catalyst particles. Next, gold was deposited on the resin sample thus abraded, and the abraded sections were observed by an electron microscope (JEOL scanning type electron microscope JSM 6060). The sections were photographed at 100× magnification, and images were obtained until the total number of particles became not less than 1500. Here, a particle in which the total of areas occupied by vacancies is not less than 1% based on a sectional area of one particle was judged to be a hollow particle. In the photographed images, the total number of all the particles and the number of the hollow particles were measured, then the number of the hollow particles was divided by the total number of all the particles, and the resulting value was multiplied by 100, whereby the hollow particle ratio was calculated.

[Reactor Damage]

A fluidized bed reactor was operated for 5 days, then the reactor was temporarily stopped, and the inner wall of the reactor was visually observed. Based on the visual observation, the reactor damage was evaluated according to the following evaluation criteria.

(Evaluation Criteria)

⊚: Any damage is not observed to the inner wall of the reactor and the sparger distributer.

○: Thickness reduction of at least a part of the inner wall of the reactor and the sparger distributer is not more than 20% of the thickness of the relevant parts.

x: Thickness of at least a part of the inner wall of the reactor and the sparger distributer is reduced by not less than 20% of the thickness of the relevant parts, or damaged portions can be confirmed.

[Evaluation of Amount Scattered]

A fluidized bed reactor was operated for 5 days, then the catalytic amount in the fluidized bed reactor was confirmed, and from a difference from the catalytic amount initially packed in the fluidized bed reactor, an average value of the amount of the catalyst scattered per day was determined. Based on the resulting amount scattered, the amount scattered was evaluated according to the following evaluation criteria.

(Evaluation Criteria)

○: The amount scattered per day is not more than 0.2% based on the catalytic amount in the reactor.

x: The amount scattered per day is more than 0.2% based on the catalytic amount in the reactor.

[Yield of Compound]

By the yield of a compound (acrylonitrile), efficiency of the reaction was evaluated. Here, the yield (%) of acrylonitrile was expressed as a percentage of the number of moles of acrylonitrile produced to the number of moles of propane fed, as shown by the following formula. Based on the yield (%) of the resulting acrylonitrile, the yield of the compound was evaluated according to the following evaluation criteria.

Acrylonitrile yield (%)=(number of moles of acrylonitrile produced/number of moles propane fed)×100

(Evaluation Criteria)
○: The yield is not less than 50%.
x: The yield is less than 50%.
[Activity (Kη) of Catalyst in Fluidized Bed Reaction]

By the activity (Kη) of the catalyst in the fluidized bed reaction, the fluidity of the catalyst was evaluated. The catalytic activity (Kη) in the evaluation of the fluidized bed reaction was defined as shown by the following formulas.

Propane conversion ratio (%)=(propane consumed (mol))/(propane fed (mol))×100

Acrylonitrile (AN) yield (%)=(acrylonitrile produced (mol))/(propane fed (mol))×100

Contact time (sec·g/cm$^3$)=($W/F$)×273/(273+$T$)

Here, W, F and T in the formula were defined as follows.
W=Amount of catalyst packed (g)
F=Mixed gas flow rate (Ncc/sec) in normal state (O° C., 1.013×10$^5$ Pa)
T=Reaction temperature (° C.)

Kη($Hr^{-1}$)=−3600/(contact time)×$ln$((100−propane conversion ratio)/100)

Here, $ln$ in the formula represents natural logarithm.
[Comprehensive Evaluation]

Based on the evaluation results of the reactor damage, the amount scattered and the acrylonitrile yield, comprehensive evaluation was carried out according to the following evaluation criteria.
(Evaluation Criteria)
○: The evaluation results of the reactor damage, the amount scattered and the acrylonitrile yield were each ○.
x: At least one of the evaluation results of the reactor damage, the amount scattered and the acrylonitrile yield was x.

Example 1

A niobium mixed solution was prepared in the following manner.

With 500 kg of water, 76.33 kg of niobic acid containing 80.2 mass % of Nb$_2$O$_5$ and 29.02 kg of oxalic acid dihydrate [H$_2$C$_2$O$_4$.2H$_2$O] were mixed. The molar ratio of oxalic acid/niobium added was 5.0, and the concentration of niobium added was 0.532 (mol-Nb/Kg-solution). This solution was heated and stirred at 95° C. for 2 hours, thereby obtaining a mixed solution containing niobium dissolved therein. This mixed solution was allowed to stand still, subjected to ice cooling and then subjected to suction filtration to filter out solids, thereby obtaining a homogeneous niobium mixed solution. From the following analysis, the molar ratio of oxalic acid/niobium in this niobium mixed solution proved to be 2.70.

In a crucible, 10 g of this niobium mixed solution was accurately weighed, dried at 95° C. overnight, and then heat-treated at 600° C. for one hour, thereby obtaining 0.7868 g of Nb$_2$O$_5$. From this result, the niobium concentration proved to be 0.592 (mol-Nb/Kg-solution).

In a 300 mL glass beaker, 3 g of this niobium mixed solution was accurately weighed, and 200 mL of hot water at about 80° C. was added, followed by addition of 10 mL of 1:1 sulfuric acid. While maintaining the solution temperature of the resulting mixed solution at 70° C. on a hot stirrer, the mixed solution was titrated using ¼ normal KMnO$_4$ with stirring. A point of time until which a faint pale pink color due to KMnO$_4$ had continued for about not shorter than 30 seconds was regarded as an end point. The concentration of oxalic acid was calculated according to the following equation using the resulting titration amount, and as a result, it was 1.573 (mol-oxalic acid/Kg-solution).

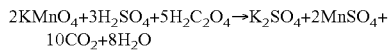

The resulting niobium mixed solution was used as a niobium mixed solution (BO) for the following catalyst preparation.
(Preparation of Composite Oxide Catalyst)

To 114.0 kg of water, 33.26 kg of ammonium heptamolybdate [(NH$_4$)$_6$Mo$_7$O$_{24}$.4H$_2$O], 4.70 kg of ammonium metavanadate [NH$_4$VO$_3$], 6.11 kg of diantimony trioxide [Sb$_2$O$_3$] and 0.41 kg of cerium nitrate were added, and while stirring, they were heated at 95° C. for one hour to obtain an aqueous starting material solution (I). Further, to 33.47 kg of the niobium mixed solution (BO), 4.49 kg of a hydrogen peroxide solution containing 30 wt % of H$_2$O$_2$ was added, and they were stirred and mixed at room temperature for 10 minutes to prepare an aqueous starting material solution (II).

After the resulting aqueous starting material solution (I) was cooled to 70° C., 59.93 kg of a silica sol containing 34.0 wt % of SiO$_2$ was added, then 7.12 kg of a hydrogen peroxide solution containing 30 wt % of H$_2$O$_2$ was further added, and stirring was continued at 55° C. for 30 minutes. Next, the aqueous starting material solution (II), 2.56 kg of an ammonium metatungstate aqueous solution containing 50.3 wt % of WO$_3$, and a dispersion obtained by dispersing 20.38 kg of a silica powder in 183.38 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 690° C. for 2 hours in a stream of nitrogen gas at a flow rate of 600 NL/min while rotating the tube, thereby obtaining a composite oxide catalyst.
(Removal of Protrusions)

In a vertical tube (inner diameter: 41.6 mm, length: 70 cm) equipped, at the bottom, with a hole-opened disc having three holes each having a diameter of 1/64 inch and provided with a paper filter at the top, 50 g of the composite oxide catalyst was introduced. At this time, a length of an air flow in the air flow direction was 52 mm, and an average linear velocity of the air flow was 310 m/s. In the composite oxide catalyst obtained after 24 hours, any protrusions was not present.

Composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was Mo$_{1.0}$V$_{0.214}$Sb$_{0.22}$Nb$_{0.107}$W$_{0.030}$Ce$_{0.005}$On/50.0 wt %-SiO$_2$.

A carbon steel fluidized bed reactor having an inner diameter of 9000 mm was packed with 140 tons of the resulting composite oxide catalyst. As the reactor, a reactor having the same structure as in FIG. 1 and having a catalyst transfer port (not shown) in the vicinity of the middle part of the reactor was used. For the packing of the reactor with the catalyst, the catalyst was transferred using air at 320° C. After the transfer, the temperature of the catalyst was 210° C.

At the position of 30 cm above the bottom surface of the catalyst packed portion (upper surface of dispersion plate 5) in the reactor, first nozzles (openings of the nozzles corresponded to first feed ports) through which a gas containing propane and ammonia was fed were installed vertically downward. The installation positions were the center of the reactor and the vertices (five in total) of a square having its center at the center of the reactor and having a length of 340 mm per side. At the bottom surface of the catalyst packed portion in the reactor, second nozzles (openings of the nozzles corresponded to second feed ports) through which a gas containing oxygen was fed were installed vertically upward. The installation positions of the second nozzles were positions (five) vertically overlapping the first nozzles through which a gas containing propane and ammonia was fed. For removal of heat of the reaction gas, four cooling coils regularly used and two cooling coils for fine temperature adjustment were installed in the internal space.

After the transfer of the catalyst was completed, air at 450° C. was introduced into the reactor to raise the temperature of the catalyst bed in the reactor up to 340° C. over a period of 12 hours. Here, feeding of ammonia gas was started, and the feed rate of ammonia was increased up to 55 Nm$^3$/hr over a period of 3 hours, and the temperature of the catalyst bed in the reactor was further raised. After the feed rate of ammonia was increased, the feed rate of air was decreased down to 280 Nm$^3$/hr. When the temperature of the catalyst bed in the reactor reached 450° C., feeding of propane was started, and the feed rate was increased up to 22.7 Nm$^3$/hr over a period of 6 hours, and at the same time, the feed rate of air was increased up to 363 Nm$^3$/hr. Here, the catalyst bed referred to a space which was located at the lower part of the internal space of the reactor and in which the special density of the catalyst was high.

Thereafter, control of the feed rate of each gas and the temperature was carried out, and at a reactor temperature of 440° C. and a reaction pressure of 50 kPa, to the reactor were fed propane and ammonia through the nozzles (first feed ports) on the upper side and air through the nozzles (second feed ports) on the lower side in a molar ratio of propane:ammonia:air=1:1:16 in such a manner that the linear velocity of the gas from the first feed ports became 45 m/s. After 5 days from the start of the reaction, the AN yield was 53.4%. Thereafter, the reactor was temporarily stopped, and its inner wall was visually observed. The results are set forth in Table 1.

Examples 2 to 4, Comparative Examples 1 and 2

The same operations as in Example 1 were carried out, except that by controlling the flow rate of the diluent nitrogen gas, the linear velocity was changed as described in Table 1. The results are set forth in Table 1.

Example 5

A catalyst for use in Example 5 was prepared in the following manner.
(Preparation of Composite Oxide Catalyst)

To 124.0 kg of water, 34.69 kg of ammonium heptamolybdate [(NH$_4$)$_6$Mo$_7$O$_{24}$.4H$_2$O], 4.88 kg of ammonium metavanadate [NH$_4$VO$_3$], 6.26 kg of diantimony trioxide [Sb$_2$O$_3$] and 0.43 kg of cerium nitrate were added, and while stirring, they were heated at 95° C. for one hour to obtain an aqueous starting material solution (I).

To 34.92 kg of the niobium mixed solution (BO) used in Example 1, 4.69 kg of a hydrogen peroxide solution containing 30 wt % of H$_2$O$_2$ was added, and they were stirred and mixed at room temperature for 10 minutes to prepare an aqueous starting material solution (II).

After the resulting aqueous starting material solution (I) was cooled to 70° C., 57.53 kg of a silica sol containing 34.0 wt % of SiO$_2$ was added, then 7.29 kg of a hydrogen peroxide solution containing 30 wt % of H$_2$O$_2$ was further added, and stirring was continued at 55° C. for 30 minutes. Next, the aqueous starting material solution (II), 2.67 kg of an ammonium metatungstate aqueous solution containing 50.3 wt % of WO$_3$, and a dispersion obtained by dispersing 19.56 kg of a silica powder in 176.04 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 680° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was Mo$_{1.0}$V$_{0.213}$Sb$_{0.221}$Nb$_{0.107}$W$_{0.030}$Ce$_{0.005}$On/48.0 wt %-SiO$_2$.

The same operations as in Example 1 were carried out, except that the above catalyst was used. The results are set forth in Table 1.

Examples 6 to 8, Comparative Example 3

The same operations as in Example 5 were carried out, except that by controlling the flow rate of the diluent nitrogen gas, the linear velocity was changed as described in Table 1. The results are set forth in Table 1.

Example 9

A catalyst was prepared in the same manner as in Example 5, except that the amount of water used to prepare the aqueous starting material solution (I) was changed to 20 kg, and the amount of water used to disperse the silica powder in the preparation of the aqueous mixed solution (III) was changed to 120 kg. The results are set forth in Table 1.

Example 10

A catalyst for use in Example 10 was prepared in the following manner.
(Preparation of Composite Oxide Catalyst)

To 141.0 kg of water, 36.69 kg of ammonium heptamolybdate [(NH$_4$)$_6$Mo$_7$O$_{24}$.4H$_2$O], 5.17 kg of ammonium metavanadate [NH$_4$VO$_3$], 6.62 kg of diantimony trioxide

[Sb$_2$O$_3$] and 0.45 kg of cerium nitrate were added, and while stirring, they were heated at 95° C. for one hour to obtain an aqueous starting material solution (I). To 36.93 kg of the niobium mixed solution (BO) used in Example 1, 4.96 kg of a hydrogen peroxide solution containing 30 wt % of H$_2$O$_2$ was added, and they were stirred and mixed at room temperature for 10 minutes to prepare an aqueous starting material solution (II).

After the resulting aqueous starting material solution (I) was cooled to 70° C., 53.93 kg of a silica sol containing 34.0 wt % of SiO$_2$ was added, then 7.71 kg of a hydrogen peroxide solution containing 30 wt % of H$_2$O$_2$ was further added, and stirring was continued at 55° C. for 30 minutes. Next, the aqueous starting material solution (II), 2.83 kg of an ammonium metatungstate aqueous solution containing 50.3 wt % of WO$_3$, and a dispersion obtained by dispersing 18.34 kg of a silica powder in 165.04 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 670° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was Mo$_{1.0}$V$_{0.213}$Sb$_{0.221}$Nb$_{0.107}$W$_{0.030}$Ce$_{0.005}$On/45.0 wt %-SiO$_2$.

The same operations as in Example 1 were carried out, except that the above catalyst was used, and by controlling the flow rate of the diluent nitrogen gas, the linear velocity was changed as described in Table 1. The results are set forth in Table 1.

Example 11, Comparative Example 4

The same operations as in Example 10 were carried out, except that by controlling the flow rate of the diluent nitrogen gas, the linear velocity was changed as described in Table 1. The results are set forth in Table 1.

Example 12

A catalyst for use in Example 12 was prepared in the following manner.
(Preparation of Composite Oxide Catalyst)

To 122.0 kg of water, 35.36 kg of ammonium heptamolybdate [(NH$_4$)$_6$Mo$_7$O$_{24}$.4H$_2$O], 4.98 kg of ammonium metavanadate [NH$_4$VO$_3$], 6.38 kg of diantimony trioxide [Sb$_2$O$_3$] and 0.44 kg of cerium nitrate were added, and while stirring, they were heated at 95° C. for one hour to obtain an aqueous starting material solution (I). To 35.59 kg of the niobium mixed solution (BO) used in Example 1, 4.78 kg of a hydrogen peroxide solution containing 30 wt % of H$_2$O$_2$ was added, and they were stirred and mixed at room temperature for 10 minutes to prepare an aqueous starting material solution (II).

After the resulting aqueous starting material solution (I) was cooled to 70° C., 51.82 kg of a silica sol containing 34.0 wt % of SiO$_2$ was added, then 7.43 kg of a hydrogen peroxide solution containing 30 wt % of H$_2$O$_2$ was further added, and stirring was continued at 55° C. for 30 minutes. Next, the aqueous starting material solution (II), 2.72 kg of an ammonium metatungstate aqueous solution containing 50.3 wt % of WO$_3$, and a dispersion obtained by dispersing 20.69 kg of a silica powder in 186.16 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 680° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was Mo$_{1.0}$V$_{0.213}$Sb$_{0.220}$Nb$_{0.107}$W$_{0.030}$Ce$_{0.005}$On/47.0 wt %-SiO$_2$.

The same operations as in Example 1 were carried out, except that the above catalyst was used, and by controlling the flow rate of the diluent nitrogen gas, the linear velocity was changed as described in Table 1. The results are set forth in Table 1.

Example 13

A catalyst for use in Example 13 was prepared in the following manner.
(Preparation of Composite Oxide Catalyst)

To 133.0 kg of water, 36.69 kg of ammonium heptamolybdate [(NH$_4$)$_6$Mo$_7$O$_{24}$.4H$_2$O], 5.17 kg of ammonium metavanadate [NH$_4$VO$_3$], 6.62 kg of diantimony trioxide [Sb$_2$O$_3$] and 0.45 kg of cerium nitrate were added, and while stirring, they were heated at 95° C. for one hour to obtain an aqueous starting material solution (I). To 36.93 kg of the niobium mixed solution (BO) used in Example 1, 4.96 kg of a hydrogen peroxide solution containing 30 wt % of H$_2$O$_2$ was added, and they were stirred and mixed at room temperature for 10 minutes to prepare an aqueous starting material solution (II).

After the resulting aqueous starting material solution (I) was cooled to 70° C., 49.62 kg of a silica sol containing 34.0 wt % of SiO$_2$ was added, then 7.71 kg of a hydrogen peroxide solution containing 30 wt % of H$_2$O$_2$ was further added, and stirring was continued at 55° C. for 30 minutes. Next, the aqueous starting material solution (II), 2.83 kg of an ammonium metatungstate aqueous solution containing 50.3 wt % of WO$_3$, and a dispersion obtained by dispersing 19.81 kg of a silica powder in 178.24 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 670° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was $Mo_{1.0}V_{0.213}Sb_{0.218}Nb_{0.107}W_{0.030}Ce_{0.005}On/45.0$ wt %-$SiO_2$. The same operations as in Example 1 were carried out, except that the above catalyst was used, and by controlling the flow rate of the diluent nitrogen gas, the linear velocity was changed as described in Table 1. The results are set forth in Table 1.

Example 14, Comparative Example 5

The same operations as in Example 13 were carried out, except that by controlling the flow rate of the diluent nitrogen gas, the linear velocity was changed as described in Table 1. The results are set forth in Table 1.

Example 15

A catalyst was prepared in the same manner as in Example 13, except that the amount of water used to prepare the aqueous starting material solution (I) was changed to 30 kg, and the amount of water used to disperse the silica powder in the preparation of the aqueous mixed solution (III) was changed to 110 kg. The results are set forth in Table 1.

Example 16

A catalyst for use in Example 16 was prepared in the following manner.
(Preparation of Composite Oxide Catalyst)
To 116.0 kg of water, 36.03 kg of ammonium heptamolybdate [$(NH_4)_6Mo_7O_{24}\cdot 4H_2O$], 5.07 kg of ammonium metavanadate [$NH_4VO_3$], 6.50 kg of diantimony trioxide [$Sb_2O_3$] and 0.44 kg of cerium nitrate were added, and while stirring, they were heated at 95° C. for one hour to obtain an aqueous starting material solution (I). To 36.26 kg of the niobium mixed solution (BO) used in Example 1, 4.87 kg of a hydrogen peroxide solution containing 30 wt % of $H_2O_2$ was added, and they were stirred and mixed at room temperature for 10 minutes to prepare an aqueous starting material solution (II).

After the resulting aqueous starting material solution (I) was cooled to 70° C., 44.11 kg of a silica sol containing 34.0 wt % of $SiO_2$ was added, then 7.57 kg of a hydrogen peroxide solution containing 30 wt % of $H_2O_2$ was further added, and stirring was continued at 55° C. for 30 minutes. Next, the aqueous starting material solution (II), 2.77 kg of an ammonium metatungstate aqueous solution containing 50.3 wt % of $WO_3$, and a dispersion obtained by dispersing 22.49 kg of a silica powder in 202.45 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 670° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was $Mo_{1.0}V_{0.212}Sb_{0.217}Nb_{0.107}W_{0.030}Ce_{0.005}On/46.0$ wt %-$SiO_2$. The same operations as in Example 1 were carried out, except that the above catalyst was used. The results are set forth in Table 1.

Examples 17 and 18, Comparative Examples 6 and 7

The same operations as in Example 16 were carried out, except that by controlling the flow rate of the diluent nitrogen gas, the linear velocity was changed as described in Table 1. The results are set forth in Table 1.

Example 18

A catalyst was prepared in the same manner as in Example 16, except that the amount of water used to prepare the aqueous starting material solution (I) was changed to 20 kg, and the amount of water used to disperse the silica powder in the preparation of the aqueous starting material solution (III) was changed to 100 kg. Further, the same operations as in Example 16 were carried out, except that by controlling the flow rate of the diluent nitrogen gas, the linear velocity was changed as described in Table 1. The results are set forth in Table 1.

Example 20

A catalyst for use in Example 20 was prepared in the following manner.
(Preparation of Composite Oxide Catalyst)
To 90.0 kg of water, 35.36 kg of ammonium heptamolybdate [$(NH_4)_6Mo_7O_{24}\cdot 4H_2O$], 4.98 kg of ammonium metavanadate [$NH_4VO_3$], 6.38 kg of diantimony trioxide [$Sb_2O_3$] and 0.44 kg of cerium nitrate were added, and while stirring, they were heated at 95° C. for one hour to obtain an aqueous starting material solution (I). To 35.59 kg of the niobium mixed solution (BO) used in Example 1, 4.78 kg of a hydrogen peroxide solution containing 30 wt % of $H_2O_2$ was added, and they were stirred and mixed at room temperature for 10 minutes to prepare an aqueous starting material solution (II).

After the resulting aqueous starting material solution (I) was cooled to 70° C., 33.80 kg of a silica sol containing 34.0 wt % of $SiO_2$ was added, then 7.43 kg of a hydrogen peroxide solution containing 30 wt % of $H_2O_2$ was further added, and stirring was continued at 55° C. for 30 minutes. Next, the aqueous starting material solution (II), 2.72 kg of an ammonium metatungstate aqueous solution containing 50.3 wt % of $WO_3$, and a dispersion obtained by dispersing 26.81 kg of a silica powder in 241.32 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 680° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was $Mo_{1.0}V_{0.214}Sb_{0.220}Nb_{0.107}W_{0.030}Ce_{0.005}O_n$/47.0 wt %-$SiO_2$. The same operations as in Example 1 were carried out, except that the above catalyst was used. The results are set forth in Table 1.

Example 21

The same operations as in Example 20 were carried out, except that by controlling the flow rate of the diluent nitrogen gas, the linear velocity was changed as described in Table 1. The results are set forth in Table 1.

Comparative Example 8

A catalyst was prepared in the same manner as in Example 20, except that the amount of water used to prepare the aqueous starting material solution (I) was changed to 150 kg, and the amount of water used to disperse the silica powder in the preparation of the aqueous starting material solution (III) was changed to 360 kg. The results are set forth in Table 1.

Example 22

A catalyst for use in Example 22 was prepared in the following manner.
(Preparation of Composite Oxide Catalyst)

To 93 kg of water, 36.69 kg of ammonium heptamolybdate [$(NH_4)_6Mo_7O_{24} \cdot 4H_2O$], 5.17 kg of ammonium metavanadate [$NH_4VO_3$], 6.62 kg of diantimony trioxide [$Sb_2O_3$] and 0.45 kg of cerium nitrate were added, and while stirring, they were heated at 95° C. for one hour to obtain an aqueous starting material solution (I).

To 36.93 kg of the niobium mixed solution (BO) used in Example 1, 4.96 kg of a hydrogen peroxide solution containing 30 wt % of $H_2O_2$ was added, and they were stirred and mixed at room temperature for 10 minutes to prepare an aqueous starting material solution (II).

After the resulting aqueous starting material solution (I) was cooled to 70° C., 26.97 kg of a silica sol containing 34.0 wt % of $SiO_2$ was added, then 7.71 kg of a hydrogen peroxide solution containing 30 wt % of $H_2O_2$ was further added, and stirring was continued at 55° C. for 30 minutes. Next, the aqueous starting material solution (II), 2.83 kg of an ammonium metatungstate aqueous solution containing 50.3 wt % of $WO_3$, and a dispersion obtained by dispersing 27.51 kg of a silica powder in 247.56 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 680° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was $Mo_{1.0}V_{0.214}Sb_{0.219}Nb_{0.107}W_{0.030}Ce_{0.005}O_n$/45.0 wt %-$SiO_2$.

The same operations as in Example 1 were carried out, except that the above catalyst was used, and by controlling the flow rate of the diluent nitrogen gas, the linear velocity was changed as described in Table 1. The results are set forth in Table 1.

Example 23

A catalyst for use in Example 23 was prepared in the following manner.
(Preparation of Composite Oxide Catalyst)

To 264 kg of water, 37.16 kg of ammonium heptamolybdate [$(NH_4)_6Mo_7O_{24} \cdot 4H_2O$], 5.24 kg of ammonium metavanadate [$NH_4VO_3$], 6.71 kg of diantimony trioxide [$Sb_2O_3$] and 0.46 kg of cerium nitrate were added, and while stirring, they were heated at 95° C. for one hour to obtain an aqueous starting material solution (I).

To 31.61 kg of the niobium mixed solution (BO) used in Example 1, 5.20 kg of a hydrogen peroxide solution containing 30 wt % of $H_2O_2$ was added, and they were stirred and mixed at room temperature for 10 minutes to prepare an aqueous starting material solution (II).

After the resulting aqueous starting material solution (I) was cooled to 70° C., 18.02 kg of a silica sol containing 34.0 wt % of $SiO_2$ was added, then 7.81 kg of a hydrogen peroxide solution containing 30 wt % of $H_2O_2$ was further added, and stirring was continued at 55° C. for 30 minutes. Next, the aqueous starting material solution (II), 2.88 kg of an ammonium metatungstate aqueous solution containing 50.3 wt % of $WO_3$, and a dispersion obtained by dispersing 18.38 kg of a silica powder in 257.10 kg of water were successively added to obtain an aqueous mixed solution (III). The aqueous mixed solution (III) was aged at 50° C. for 2 hours and 30 minutes after the addition of the aqueous starting material solution (II), thereby obtaining a slurry. The resulting slurry was fed to a centrifugal spray dryer and dried, thereby obtaining a microspherical dry powder. The air temperature at the inlet of the dryer was 210° C., and the air temperature at the outlet thereof was 120° C. This step was repeated several times, and the resulting dry powder was packed in a SUS cylindrical calcining tube having an inner diameter of 500 mm, a length of 3500 mm and a wall thickness of 20 mm, and calcined at 680° C. for 2 hours in a stream of nitrogen gas at a flow rate of 600 NL/min while rotating the tube, thereby obtaining a composite oxide catalyst.

Protrusions were removed in the same manner as in Example 1, and composition of the composite oxide catalyst was measured by an X-ray fluorescence analysis (Rigaku RINT1000, Cr tubular bulb, tube voltage: 50 kV, tube current: 50 mA). The composition of the resulting composite oxide catalyst was $Mo_{1.0}V_{0.214}Sb_{0.219}Nb_{0.107}W_{0.030}Ce_{0.005}O_n/40.0$ wt%-$SiO_2$.

The same operations as in Example 1 were carried out, except that the above catalyst was used, and by controlling the flow rate of the diluent nitrogen gas, the linear velocity was changed as described in Table 1. The results are set forth in Table 1.

Comparative Example 9

The same operations as in Example 23 were carried out, except that by controlling the flow rate of the diluent nitrogen gas, the linear velocity was changed as described in Table 1. The results are set forth in Table 1.

TABLE 1

| | ATT % | LV m/s | Hollow particle ratio % | Reactor/tube damage | Amount scattered Ratio % | Evaluation | Actylonitrile yield % | Evaluation | Comprehensive evaluation | Activity (Kη) |
|---|---|---|---|---|---|---|---|---|---|---|
| Ex. 1 | 1 | 45 | 3 | ◎ | 0.04 | ○ | 53.4 | ○ | ◎ | 3.0 |
| Ex. 2 | 1 | 75 | 3 | ○ | 0.05 | ○ | 53.6 | ○ | ○ | 2.9 |
| Ex. 3 | 1 | 100 | 3 | ○ | 0.06 | ○ | 53.4 | ○ | ○ | 2.8 |
| Comp. Ex. 1 | 1 | 120 | 3 | X | 0.05 | ○ | 53.8 | ○ | X | 2.6 |
| Ex. 4 | 1 | 10 | 3 | ○ | 0.01 | ○ | 52.8 | ○ | ○ | 3.1 |
| Comp. Ex. 2 | 1 | 3 | 3 | ○ | 0.01 | ○ | 49.0 | X | X | 2.6 |
| Ex. 5 | 2 | 45 | 5 | ◎ | 0.04 | ○ | 53.5 | ○ | ◎ | 3.0 |
| Ex. 6 | 2 | 75 | 5 | ○ | 0.04 | ○ | 53.5 | ○ | ○ | 2.9 |
| Ex. 7 | 2 | 90 | 5 | ○ | 0.06 | ○ | 52.8 | ○ | ○ | 2.8 |
| Ex. 8 | 2 | 120 | 5 | ○ | 0.07 | ○ | 53.3 | ○ | ○ | 2.7 |
| Ex. 9 | 2 | 120 | 21 | ○ | 0.07 | ○ | 52.8 | ○ | ○ | 2.2 |
| Comp. Ex. 3 | 2 | 130 | 5 | X | 0.06 | ○ | 53.6 | ○ | X | 2.7 |
| Ex. 10 | 4 | 90 | 9 | ○ | 0.06 | ○ | 53.0 | ○ | ○ | 2.6 |
| Ex. 11 | 4 | 105 | 9 | ○ | 0.11 | ○ | 52.6 | ○ | ○ | 2.7 |
| Comp. Ex. 4 | 4 | 160 | 9 | X | 0.14 | ○ | 53.2 | ○ | X | 2.7 |
| Ex. 12 | 6 | 90 | 10 | ○ | 0.07 | ○ | 53.0 | ○ | ○ | 2.7 |
| Ex. 13 | 10 | 75 | 12 | ○ | 0.06 | ○ | 53.5 | ○ | ○ | 2.7 |
| Ex. 14 | 10 | 90 | 12 | ○ | 0.12 | ○ | 53.2 | ○ | ○ | 2.6 |
| Ex. 15 | 10 | 130 | 25 | ○ | 0.15 | ○ | 52.7 | ○ | ○ | 2.1 |
| Comp. Ex. 5 | 10 | 150 | 12 | ○ | 0.21 | X | 52.5 | ○ | X | 2.5 |
| Ex. 16 | 20 | 45 | 15 | ○ | 0.07 | ○ | 53.4 | ○ | ○ | 2.6 |
| Ex. 17 | 20 | 75 | 15 | ○ | 0.09 | ○ | 53.5 | ○ | ○ | 2.5 |
| Ex. 18 | 20 | 100 | 30 | ○ | 0.10 | ○ | 52.8 | ○ | ○ | 2.0 |
| Comp. Ex. 6 | 20 | 120 | 15 | ○ | 0.25 | X | 53.1 | ○ | X | 2.4 |
| Ex. 19 | 20 | 10 | 15 | ○ | 0.03 | ○ | 52.6 | ○ | ○ | 2.5 |
| Comp. Ex. 7 | 20 | 3 | 15 | ○ | 0.01 | ○ | 47.0 | X | X | 2.3 |
| Ex. 20 | 30 | 45 | 35 | ○ | 0.11 | ○ | 52.7 | ○ | ○ | 2.0 |
| Ex. 21 | 30 | 30 | 35 | ○ | 0.05 | ○ | 53.1 | ○ | ○ | 1.9 |
| Comp. Ex. 8 | 30 | 100 | 17 | ○ | 0.22 | X | 52.7 | ○ | X | 2.5 |
| Ex. 22 | 35 | 30 | 17 | ○ | 0.10 | ○ | 53.0 | ○ | ○ | 2.6 |
| Ex. 23 | 50 | 10 | 19 | ○ | 0.05 | ○ | 52.3 | ○ | ○ | 2.3 |
| Comp. Ex. 9 | 50 | 45 | 19 | ○ | 0.22 | X | 52.4 | ○ | X | 2.5 |

The present application is based on Japanese patent application (Japanese Patent Application No. 2017-119459) filed with Japan Patent Office on Jun. 19, 2017, and the contents thereof are incorporated herein by reference.

INDUSTRIAL APPLICABILITY

The present invention has industrial applicability as a process for producing a compound such as an unsaturated acid or unsaturated nitrile.

REFERENCE SIGNS LIST

1: fluidized bed reactor, 2: catalyst, 3: internal space, 4: starting material feed port, 5: dispersion plate, 6: discharge port, 7: cyclone, 7$a$: inlet, 8: dispersion tube, 9: feed port, 20: apparatus for measuring the degree of abrasion resistance, 21: hole-opened disc, 21$a$: orifice, 22: vertical tube, 23: catalyst, 24: conical part, 25: cylinder, 26: opening, A: starting material gas, B: oxygen-containing gas, C: reaction product gas

The invention claimed is:

1. A process for producing a compound by use of a fluidized bed reactor comprising an internal space having a catalyst housed in a fluidizable manner therein, a first feed port into which a starting material gas comprising a hydrocarbon is fed to the fluidized bed reactor, a second feed port into which an oxygen-containing gas comprising oxygen is fed to the fluidized bed reactor, and a discharge port into which a reaction product gas is discharged from the fluidized bed reactor, comprising a reaction step of subjecting the hydrocarbon to a vapor phase catalytic oxidation reaction or a vapor phase catalytic ammoxidation reaction in the presence of the catalyst in the internal space to produce the corresponding unsaturated acid or unsaturated nitrile, respectively, wherein in the reaction step, a linear velocity (m/sec) of the starting material gas at the first feed port is adjusted against a degree of abrasion resistance (%) of the catalyst so as to satisfy the condition represented by the following expression (1) or (2):

condition (1): when the degree of abrasion resistance (%) of the catalyst is not less than 0 and not more than 4, $$5 \leq \text{linear velocity (m/sec)} \leq 12.5 \times \text{degree of abrasion resistance (\%)} + 100$$

condition (2): when the degree of abrasion resistance (%) of the catalyst is more than 4 and not more than 62, $$5 \leq \text{linear velocity (m/sec)} \leq -2.5 \times \text{degree of abrasion resistance (\%)} + 160, \text{ and}$$

wherein a hollow particle ratio (%) of the catalyst is not more than 25%.

2. The process for producing the compound according to claim 1, wherein the degree of abrasion resistance (%) is not less than 1 and not more than 10.

3. The process for producing the compound according to claim 1, wherein the hydrocarbon is an alkane and/or an alkene.

* * * * *